(12) United States Patent
Gatto et al.

(10) Patent No.: US 11,147,891 B1
(45) Date of Patent: Oct. 19, 2021

(54) REUSABLE STRAW AND CASE WITH INTEGRATED CLEANING, DRYING AND SANITIZING MEMBER

(71) Applicants: James Gatto, Vienna, VA (US); Meggan Maromonte, Vienna, VA (US)

(72) Inventors: James Gatto, Vienna, VA (US); Meggan Maromonte, Vienna, VA (US)

(*) Notice: Subject to any disclaimer, the term of this patent is extended or adjusted under 35 U.S.C. 154(b) by 278 days.

(21) Appl. No.: 16/516,203

(22) Filed: Jul. 18, 2019

(51) Int. Cl.
| | |
|---|---|
| *A61L 2/10* | (2006.01) |
| *A45C 11/24* | (2006.01) |
| *A45C 15/00* | (2006.01) |
| *A61L 2/24* | (2006.01) |
| *A61L 2/04* | (2006.01) |
| *A47G 21/18* | (2006.01) |

(52) U.S. Cl.
CPC ............ *A61L 2/10* (2013.01); *A45C 11/24* (2013.01); *A45C 15/00* (2013.01); *A61L 2/04* (2013.01); *A61L 2/24* (2013.01); *A47G 21/18* (2013.01); *A61L 2202/11* (2013.01); *A61L 2202/14* (2013.01); *A61L 2202/17* (2013.01)

(58) Field of Classification Search
CPC ..... A61L 2/10; A61L 2/04; A61L 2/24; A61L 2202/17; A61L 2202/14; A61L 2202/11; A45C 15/00; A45C 11/24; A47G 21/18
USPC .................................................. 250/455.11
See application file for complete search history.

(56) References Cited

U.S. PATENT DOCUMENTS

| | | | |
|---|---|---|---|
| 3,189,171 A | 7/1965 | Miller | |
| 4,171,401 A * | 10/1979 | Legrix | A01K 1/0152 428/17 |
| 4,909,437 A | 3/1990 | Kang | |
| 5,148,971 A | 9/1992 | Ahn | |
| 5,852,879 A | 12/1998 | Shumaier | |
| 6,019,543 A | 2/2000 | Junker | |
| 6,753,537 B2 | 6/2004 | Woo | |
| 8,403,172 B1 | 3/2013 | Kelley | |
| 9,107,523 B1 * | 8/2015 | Goldsmith | F25D 3/14 |
| 10,123,614 B2 | 11/2018 | Pepper | |

* cited by examiner

*Primary Examiner* — Kiet T Nguyen
(74) *Attorney, Agent, or Firm* — Duncan Galloway Egan Greenwald PLLC; Kevin T. Duncan

(57) ABSTRACT

The invention relates to a personal, reusable straw and a case comprising a holder for the straw, where the case comprises elements to flush, wash, clean, sanitize, and/or dry the straw in the holder. A pump may pump fluid from a fluid reservoir to lead fluid into and/or around the straw. A fan may blow air to the straw for drying the outside and/or inside of the straw. A heating element may dry the straw. A UV or other light source may provide light which is directed to sanitize the outer and inner surfaces of the straw. A controller in the case may control these elements. The controller may include a wireless transceiver for communication with a mobile application to enable a user to control the elements manually and/or via a program.

20 Claims, 12 Drawing Sheets

REUSABLE STRAW AND CASE WITH INTEGRATED CLEANING, DRYING AND SANITIZING MEMBER

FIELD OF THE INVENTION

A personal, reusable straw and a case for the straw with an integrated cleaning, drying and/or sanitizing member.

BACKGROUND OF THE INVENTION

The National Park Service has estimated that nearly 500 million plastic straws are used per day in the US alone. See https://www.nps.gov/articles/straw-free.htm (last visited Jul. 18, 2019). As a result, there is a growing movement for restaurants and other food service establishments to scale back on the use of plastic straws. Various establishments have switched to paper straws, which are undesirable to some users. Various other alternatives have been proposed. Each has some drawbacks.

One proposal is for personal reusable straws, for example, a solid cylindrical straw made of fixed length and made of metallic material. These too have various drawbacks, one of which relates to the difficulty and/or inconvenience of cleaning them between uses.

While it may be possible in some locations to rinse the straw with water after use (e.g., using a bathroom faucet in a restaurant), this leads to other problems. One problem relates to the difficulty of drying the straw after rinsing. In particular, it may be difficult to dry the inside of the straw after it is rinsed.

Another concern relates to sanitary aspects. Merely rinsing a straw with water will not necessarily sanitize the straw. For example, if a straw is used to drink a cola product, sugars and other residue may remain inside the straw. Even if a straw is rinsed, if water is left inside the straw, due to the inability to dry it, this can further lead to unsanitary conditions. For example, putting a wet straw into a purse is not likely to be the most hygienic practice.

Currently, straws come in different sizes and lengths. Carrying a relatively long metallic straw in a pocket or purse may be inconvenient. Other drawbacks exist. Existing straw designs include TELESCOPING STRAW ASSEMBLY FOR DRINKING BEVERAGES, Kang, U.S. Pat. No. 4,909,437, issued Mar. 20, 1990; COMPACT DRINKING STRAW, Miller, U.S. Pat. No. 3,189,171, issued Jun. 15, 1965; MULTISTAGE TELESCOPIC TYPE STRAW, Keisuke Nishida, Japanese Pat. No. 6019543B2, issued Nov. 11, 2016; BEVERAGE CARTON WITH TELESCOPIC FLOATING STRAW, Ahn, U.S. Pat. No. 5,148,971, issued Sep. 22, 1992; COLLAPSIBLE, SANITIZED STRAW ASSEMBLY, Kelley et al., U.S. Pat. No. 8,403,172, issued Mar. 26, 2013; and REUSABLE FOLDABLE DRINKING STRAW IN STORAGE CASE, Pepper, U.S. Pat. No. 10,123,614, issued Nov. 13, 2018; each of which is incorporated by reference herein in their entirety.

Existing methods for sterilizing the external surface of other objects include PORTABLE TOOTHBRUSH CASE WITH UV LAMP, Woo, U.S. Pat. No. 6,753,537, issued Jun. 22, 2004; and MOISTURE SENSATIVE ITEM DRYING APPLIANCE, Shumaier, U.S. Pat. No. 5,852,879, issued Dec. 28, 1998, both of which are incorporated by reference herein in their entirety. These solutions address different problems for objects that differ from those of the present invention.

Some personal straws are packaged with pipe cleaners or brushes. These items themselves can become dirty and do not necessarily sanitize or dry the straws.

Existing tools and techniques for cleaning a personal, reusable straw are lacking and/or fail to provide effective results for one or more reasons.

SUMMARY OF THE INVENTION

Various aspects of the invention address one or more of these and/or other problems or drawbacks with known straws.

One aspect of the invention is to provide a personal, reusable straw and a case for the straw, where the case cleans, dries and/or sanitizes the straw. The case may include a holder for the straw. The case may include an integrated cleaning, drying and/or sanitizing member which provides for the flushing of fluid over (the outside surface) and/or through (the inner portion) of the straw to wash it, the sanitizing of the straw by UV light (or other sanitizing mechanism), and/or the drying of the straw by the movement of air and/or by heat.

The straw can include a variety of features to enable it to be conveniently used, carried and cleaned. The straw may have various configurations, shapes, sizes and features. By way of example, the straw may be substantially cylindrical of a fixed length or variable length (e.g. telescoping) and fixed diameter or variable diameter. It can be made of various materials including stainless steel or other metallic material, glass or other non-metallic material.

For sanitary purposes and convenience, a case for the straw may be provided. The case may be customized based on the characteristics of a straw that it is designed to hold. For example, the case may comprise an outer case and at least an inner portion sized and configured to hold the straw in a relatively fixed position within the case. For example, the inner portion may include a material that includes a channel configured to closely follow the contours of the straw when the straw is located in a storage position as described below. Various other mechanisms for holding the straw in the case may be used. The holder in the inner portion of the case may hold the straw in place by using a contoured shape, a set of plastic or metallic clips, a set of rubber grommets, a magnet, and/or other suitable securing mechanisms.

According to another feature, the case may have one or more mechanisms for cleaning, drying and/or sanitizing the straw when located therein. For example, within a portion of the case, an elongated brush may be provided for cleaning the straw. Alternatively, or in addition thereto, the case may have a fluid reservoir and a pump that is configured to circulate a fluid through the inner portion of the straw and/or around the outer surface of the straw when the straw is located in the holder therein to wash or flush the straw with a fluid. The fluid, if used, may be a liquid, such as water, distilled water or a cleaning solution, or may be a vapor (e.g., steam) and/or a gas. The fluid may be a liquid solvent and/or a solution (e.g., comprising a solvent and one or more suitable detergents, cleaning solutions, or disinfecting agents).

One or more heating elements may be selectively operable under control of a controller and may be located within the case to facilitate drying the straw. Alternatively, or in addition thereto, a fan or other mechanism for circulating air within the holder may be selectively operable under control of a controller and may be provided to dry a straw located therein. A heating element may be selectively operable under control of a controller to heat air that is circulated (e.g., by the fan) within the holder to dry a straw located therein. A heating element may be selectively operable under control of a controller to heat fluid that is circulated (e.g., by the pump) through or around the straw to help clean the straw.

A sanitizing element (e.g., a UV or other type of light source or other sanitizing element) may be selectively operable under control of a controller and may be provided within the case to clean and/or sanitize the straw when located in the holder therein. For example, UV-C light may be used. Other forms of UV, electromagnetic energy and/or or heat may also be used. The light or other energy may impinge on the outer surface of the straw and/or at least a portion may be purposefully directed (e.g. using one or more reflectors) to the inside surface of the straw. In some situations, without providing reflectors, insufficient light may reach the inner surface of the straw. This is a functional and structural distinction from, and provides advantages over, other cases with UV light, for example, those that are only designed to irradiate the outer surface of a device (e.g., a phone).

The fluid may be recirculated and reused in the case. If so, one or more filters or other mechanisms may be used in the fluid flow path to clean/recycle the fluid.

In some cases, the fluid may be introduced around the outer surface of the straw and/or into the inside of the straw. Fluid may be directed inside the straw via a nozzle that is inserted into an end of the straw when located in the holder. The nozzle and flow rate may be adjustable to impart selected flow conditions (e.g., a jet, a spray, a pulsating flow and/or other flow conditions). If desired the straw may be located within a conduit that surrounds the straw so that fluid can be guided to and directed around the outer surface of the straw without the fluid filling the case. At the end of the conduit a guide or other structure can lead the fluid away from the straw and to a tube (or other structure) in a flow path to a spent fluid reservoir or through a filter to the fluid reservoir). A pump (e.g., a micro pump) or other mechanism may be selectively operable under control of a controller to cause the fluid to flow from the reservoir to the straw with the desired flow characteristics. In some cases, the pump may cause a continuous flow of the fluid for a period of time or may pulse the flow to create a pulsating jet of fluid. Other flow controls and/or combination of flows may be selected.

In some cases, merely impinging UV or other energy on the outer surface of the straw may be insufficient. To address this, the holder may include one or more reflective surfaces to reflect or otherwise purposefully direct enough UV light or other energy inside the straw to sanitize the inner walls of the straw. Causing both the interior and exterior surfaces of the straw to be exposed to sufficient UV light or other energy to facilitate the entire straw (inside and out) being sanitized by the UV light or other energy. Many prior art devices with UV light merely direct the light to the exterior surface of the device to be sanitized.

The UV light characteristics (e.g., frequency, wavelength range, durations and other characteristics) can be controlled by one or more controllers located in or associated with the case. One or more user control elements and a display may be provided on or in the case.

A mobile application be provided and may communicate with the controller (e.g., via Bluetooth, WIFI or other wireless communication technique) to enable user control of the internal mechanisms (e.g., pump, fan, heater, light, power and/or other mechanisms) and/or to provide information to the user about the status of the case, the processes and other information associated therewith.

The case may include various configurations. The case may provide an enclosure for the straw and other included mechanisms (e.g., brush, reservoir, pump, fan, heater, light, power and/or other mechanisms). The enclosure may be sufficiently sealed, such as by one or more O-rings or other sealing mechanisms, to prevent or substantially prevent the UV-C or other electromagnetic radiation from leaking outside the enclosure. The case may have a suitable insulation layer (e.g., on or near the inner surface of the case or elsewhere), to prevent the outer surface of the case from getting too hot if a heating element is used in the case.

In one embodiment one or more conduits may feed into the input of a manifold, the output of which may be a conduit, nozzle and or other structure that is inserted into and/or around an end of the straw. The manifold may have one or more micro valves controlled by the controller to selectively control the fluid paths operable therethrough. For example, one conduit may lead from the fluid reservoir to provide fluid to the straw. Another may lead air (e.g., from the fan) to the straw for drying the outside and/or inside of the straw. A complimentary manifold may be provided at the output end of the straw to selectively lead fluid back to a fluid reservoir without allowing air to flow thereto. The conduit, nozzle and or other structure that leads fluid to the straw may have two fluid flow portions, one portion which directs fluid around the outer surface of the straw and one portion which directs fluid through the inner portion of the straw. The nozzle or other inlet device for the straw may also have one or more other portions (e.g., to direct air into and/or around the straw).

In one embodiment, the present invention provides a straw and a holder for the straw, comprising: a straw having a predetermined contour, for example, an elongated, substantially cylindrical tube having an outer diameter and an inner diameter; and a holder comprising: an outer case; an inner portion, having a channel therein, configured to conform to the contour of the straw; and at least one mechanism located therein to clean the straw when located within the holder; at least one mechanism located therein to dry the straw when located within the holder; and/or at least one mechanism located therein to sanitize the straw when located within the holder. Three separate mechanisms may be used clean, dry and/or sanitize the straw within the holder. Alternatively, a single mechanism may perform two or all three functions.

The straw may have a variable length. The straw may have a variable inner diameter. The straw may have at least one retractable member to enable the length of the straw to be variable. The straw may have a mechanism to lock the straw at a desired length. The straw may have one or more removable sections to vary the length of the straw. The straw may have at least a first portion and a second portion, having complimentary threaded sections to enable the first portion to be removed from the second portion. The straw may have a mechanism to vary the inner diameter of the straw. The straw may have a mechanism to lock the straw at a desired inner diameter. The straw may have a mechanism to permit a first portion of the straw to be rotated with respect to at least one other portion to form an angle therebetween. The straw may have a mechanism to permit a first portion of the straw to be rotated with respect to at least one other portion to form a range of angles therebetween. The straw may have a mechanism to lock the straw at a desired angle. The straw may have a variable length and a variable inner diameter. The straw may have a variable length and at least a first portion rotatable with respect to a second portion to form and variable angle therebetween. The straw may comprise a stainless steel or other metal material, a non-metallic material, a plastic material, a non-plastic material, glass or other material. The material may be a relatively rigid material that substantially prevents the straw from being bent or may be a material configured to permit bending.

The holder may comprise a cleaning mechanism. The holder may comprise a drying mechanism. The holder may comprise a sanitizing mechanism. The holder may comprise a cleaning mechanism and a drying mechanism. The holder may comprise a cleaning mechanism and a sanitizing mechanism. The holder may comprise a drying mechanism and a sanitizing mechanism. The holder may comprise a cleaning mechanism, a drying mechanism and a sanitizing mechanism. The holder may comprise a cleaning mechanism, including a brush. The holder may comprise a cleaning mechanism other than a brush, including a fluid reservoir. The fluid can be heated by the heating mechanism. The holder may comprise a cleaning mechanism, including a fluid reservoir configured to circulate a fluid through a straw located within the holder. Used fluid can be sent to spent fluid reservoir or can be recirculated. If recirculated, a filter or other mechanism can be used to recycle the fluid.

The holder may comprise a drying mechanism including a heating element. The holder may comprise a drying mechanism including an air circulating element configured to circulate air within the holder. The holder may comprise a drying mechanism including an air circulating element and a heater to heat the air that circulates within the holder. The holder may comprise a sanitizing mechanism (for example a UV light source) within the case to clean and/or sanitize a straw located within the holder.

The holder may further comprise one or more reflective elements on one or both ends of the holder. The reflective ends may be configured to purposefully direct UV light or other radiation into the interior of the straw onto the interior straw surfaces from a single UV light source. The reflective ends may also be configured to reflect light over the entire exterior surface of the straw in the holder from a single UV light source or multiple sources. Reflecting light using one or more reflectors may be beneficial where the straw is comprised of material that does not permit UV or other light to pass through the outer layer or surface to the inner layer or surface. This permits sufficient UV light to irradiate the inner surface of the straw.

The case may further comprise a controller (e.g., a programmable controller) for controlling electronic elements of the case. The controller and other electronic elements may be in electronic communication via a logic bus. Power may be provided to the controller and other electronic elements via a power bus. A battery may be charged via a charging port and control over the battery charging and discharging rates may be controlled by the programmable controller. The programmable controller may further comprise or be in electrical communication with a memory for storing computer executable code. The memory may comprise computer executable code and/or one or more computer modules comprising logic, configurations, firmware, or instructions for operating or controlling one or more electronic elements in the case. The case may further comprise a wireless transceiver for communicating wirelessly with an external device that has a wireless transceiver, such as a tablet, cellular telephone, personal computer or other wireless communication enables device. The external device may comprise a display capable of displaying an application comprising a graphical user interface for presenting user interface elements associated with commands and functions for operating or configuring one or more elements of the case. The case may further comprise one or more manual or physical controls for operating or configuring one or more elements of the case and may also comprise a display adapted to provide an indication to the user as to the current status of the case and/or any element thereof.

BRIEF DESCRIPTION OF THE DRAWINGS

In order to facilitate a fuller understanding of the present invention, reference is now made to the accompanying drawings, in which like elements are referenced with like numerals. These drawings should not be construed as limiting the present invention but are intended to be exemplary and for reference.

DETAILED DESCRIPTION

The present invention is not to be limited in scope by the specific embodiments described herein. It is fully contemplated that other various embodiments of and modifications to the present invention, in addition to those described herein, will become apparent to those of ordinary skill in the art from the foregoing description and accompanying drawings. Thus, such other embodiments and modifications are intended to fall within the scope of the following appended claims. Further, although the present invention has been described herein in the context of particular embodiments and implementations and applications and in particular environments, those of ordinary skill in the art will appreciate that its usefulness is not limited thereto and that the present invention can be beneficially applied in any number of ways and environments for any number of purposes or in any number of markets. Accordingly, the claims set forth below should be construed in view of the full breadth and spirit of the present invention as disclosed herein.

Figure 1:
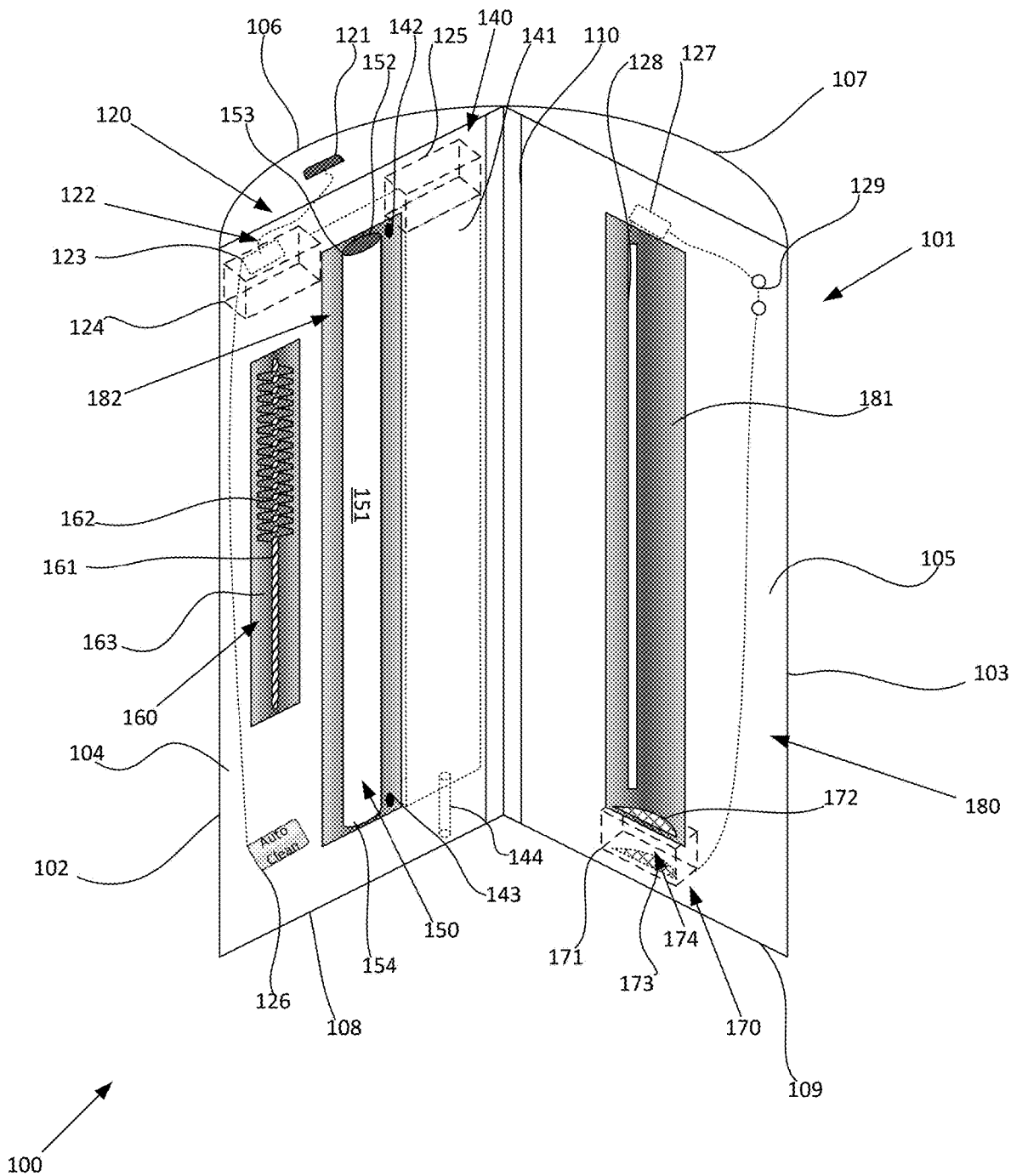
FIGS. 1 and 2 provide top perspective views of an embodiment of a personal, reusable straw and a case comprising a holder for the straw, where the case and holder clean, dry and/or sanitize the straw according to the present invention.

With reference now to FIG. 1, a top perspective view of an embodiment of a personal, reusable straw system 100 and a case 101 for the straw 150, where the case 101 cleans, dries and/or sanitizes the straw 150. The system 100 comprises the case 101 and the straw 150. The case 101 may comprise a first side 102 and a second side 103 forming a clamshell type enclosure. Other shapes and configurations may be used. The first side 102 and second side 103 may be hinged on hinge assembly 110. The first side 102 may have a top 106 and a bottom 108, and the second side 103 may have a top 107 and a bottom 109. The case 101 may further comprise an interior 180 with a first interior side 104 and a second interior side 105.

The straw 150 may comprise a body 151, a top opening 153, bottom opening 154, an exterior wall and an interior wall 152. When stored in the case, the straw 150 may be at least partially disposed within the interior 180 of the case 101 in a first channel 182 having a shape that corresponds to that of the straw 150. The first channel 182 and second channel 181 are formed in the respect first interior side 104 and second interior side 105 and may comprise the holder for the straw 150. The first channel 182 in the first interior side 104 may have a corresponding second channel 182 on the second interior side 105 that also conforms to the shape of the straw 150.

The straw 150 may be comprised of a metal, plastic, glass, acrylic or other suitable non-metal material, non-plastic material, or other material, or a combination of such materials. The case 101 may be comprised of a metal, plastic, or other suitable non-metal or non-plastic material or a combination of materials.

According to one example, the straw 150 may include at least one retractable member to enable the length of the straw to be variable. If the length of the straw is variable, it may include a mechanism to lock the straw at a desired length while in use. Instead of telescoping, the straw may include one or more removable sections (e.g., by unscrewing complimentary threaded sections of adjacent sections). The straw may include at least one mechanism to vary the diameter of the straw to accommodate user preferences and to facilitate use with drinks having different fluid characteristics. If the diameter of the straw is variable, it may include a mechanism to lock the straw at a desired diameter while in use in a known manner.

The straw may be substantially linear over its length or it may have one or more mechanism (e.g., a hinge) to permit a portion of the straw to be rotated with respect to at least one other portion to form an angle (or potential range of angles) therebetween. If the angle of the straw is variable, it may include a mechanism to lock the straw at a desired angle while in use in a known manner.

According to various alternatives, the straw may include various permutations of the following features. The straw can be telescoping or otherwise configured to vary the length of the straw, configured to have a variable inner diameter and/or hinged or otherwise configured to enable various angles.

The case 101 may further comprise other components to clean, dry and/or sanitize the straw 150 when located in the case 101. The other components may include an electronics assembly 120, a fluid washing assembly 140, optionally, a brush assembly 160, a drying assembly 170, a sanitizing mechanism (e.g., UV light 127 and/or other mechanisms).

The electronics assembly 120 may comprise some or all of the electrical systems in the case 101. The systems in the electronics assembly 120 may be connected in electrical communication with one another by connecting wires 122 and/or wireless communication. Electrical contacts 129 may be used to transfer electrical voltage and signals between the two sides of the case 101 to complete the communications and power circuits of the electronics assembly 120. Alternatively, electrical wires may be run between the two sides of the case 101.

The electronics assembly 120 may include a controller and/or other components for controlling and/or powering the mechanisms for cleaning, sanitizing and drying the straw 150. The electronics assembly 120 may comprise a control board 123 which controls and regulates all elements of the electronics assembly 120.

The control board 123 may include a controller and logic circuitry for operating and controlling the various components, including for example charging battery 124 (e.g., via charge port 121), for operating the pump 125, for operating the UV light 127, for operating the heating element 128, for operating the drying assembly 170 and/or other components. When connected to a charging source, a voltage is supplied through the charge port 121 to the battery 124 via the control board 123, which regulates charging and discharging the battery 124. Other electrical configurations may be used. The location of the components need not be as depicted. For convenience the control board 123 may also be referred to as a controller.

The fluid washing assembly 140 may comprise a fluid reservoir 141 and a pump 125 and may circulate a fluid (e.g., water, distilled water, a cleaning solution or other fluid) through the channels 181 and 182 and straw 150 via the fluid inlet 142 and fluid outlet 143. The fluid may be directed to pass through the interior of the straw 150, around the exterior of the body 151, or both. The reservoir 141 may be filled via a suitable fill port 144 or otherwise. The fluid in the reservoir may be circulated by the pump 125. The fluid in the reservoir 141 may be circulated through the straw 150 by the pump 125. The action of the fluid passing through and over the straw 150 washes and/or flushes the straw 150. The used fluid may be returned to the reservoir 141 or be collected in a used fluid reservoir such as the spent fluid reservoir 816 shown in FIG. 8. The fluid reservoir can be sized to hold enough fluid to run a desired number of cleaning cycles. If the used fluid is returned to the reservoir 141, one or more filters recycling mechanisms and/or other fluid washing mechanisms, such as the filter 817 shown in FIG. 8, can be located in the flow path.

Figure 8:
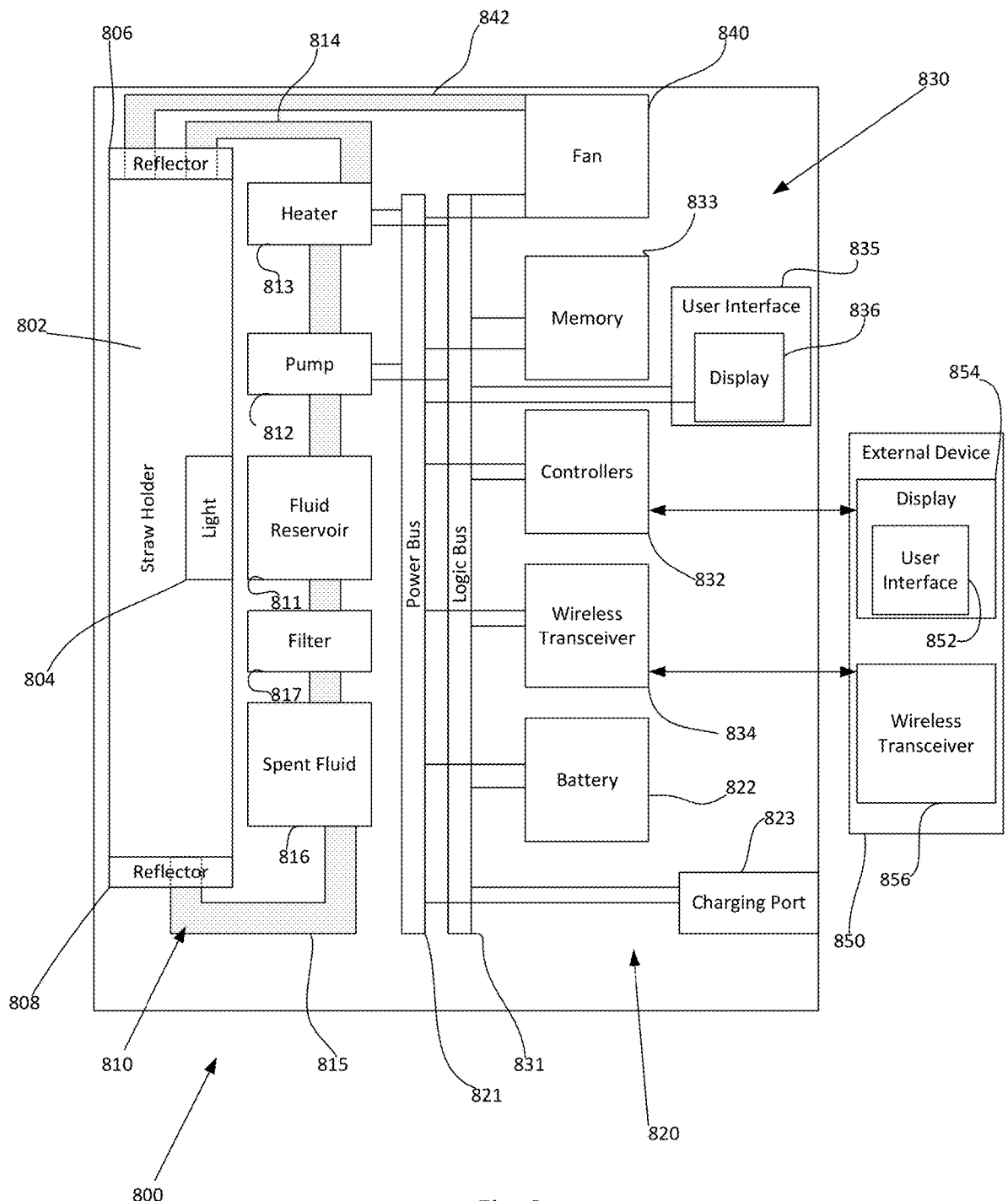
FIG. 8 provides a block diagram view of the case and holder for the personal, reusable drinking straw according to the present invention.

One or more heater element, such as the heater 813 shown in FIG. 8, may be located in the case 101. The heater elements may be located in or in proximity to the reservoir 141, the fluid flow path from the reservoir to the straw or otherwise in a position to heat the fluid to further its effectiveness and/or to generate steam or other heated fluid. The heater element may be used to dry the straw after passing fluid therethrough.

The pump 125 may be controlled by the controller 103 to operate in a continuous flow mode for a period of time or in a pulsating mode to pulse jets of fluid around and/or through the straw 150. The fluid inlet 142 and/or fluid outlet 143 may further comprise valves, nozzles, a manifold (as described herein) or other flow control devices such as one-way valves (e.g., one-way silicone valves) or may include valves controlled by solenoids operated by the control board 123 to direct fluid into, around and/or from the straw.

Figure 7:
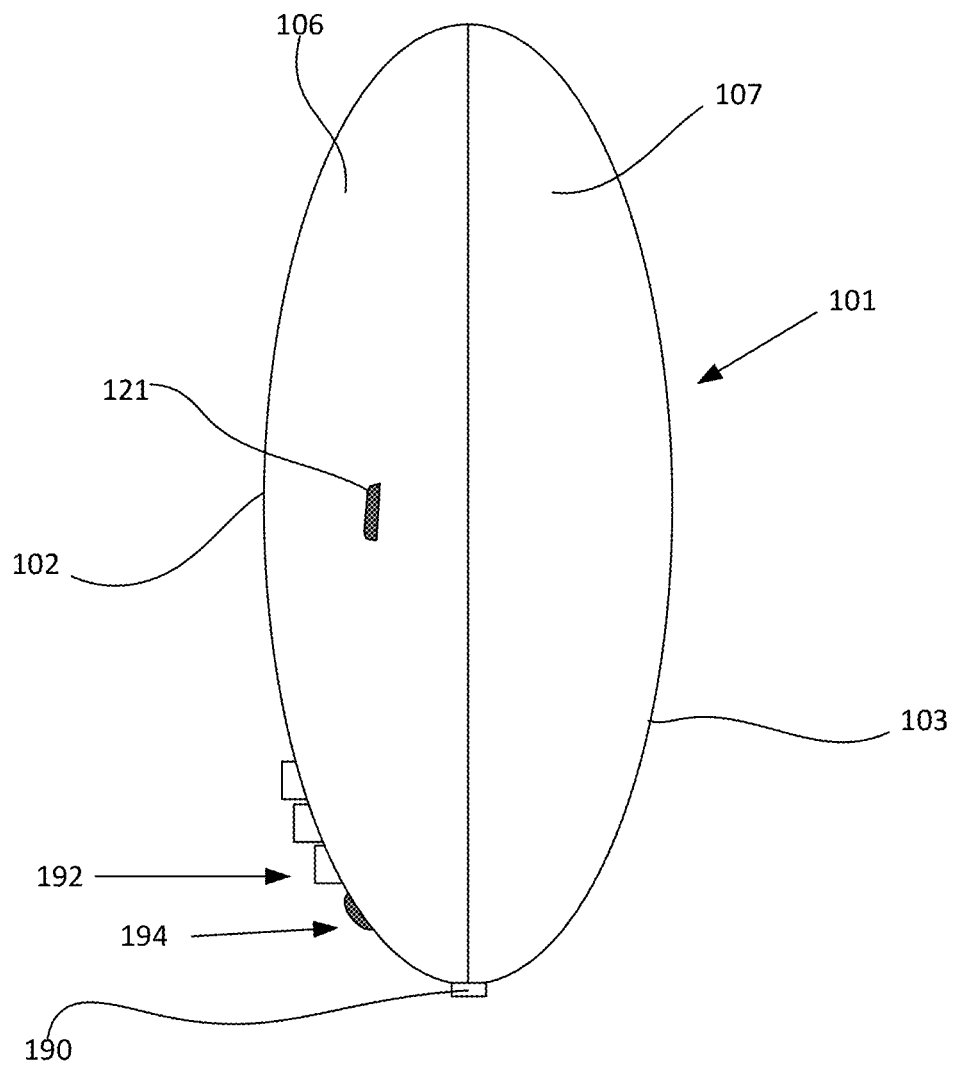
FIG. 7 provides a top view of an embodiment of the case for the personal, reusable drinking straw according to the present invention.

The fluid washing cycle may be initiated by operating a control switch such as the button 126 or may be operated by an exterior button or control, as shown in FIG. 7.

Cleaning may be further be aided by a UV light 127 which may emit light at a wavelength adapted to neutralize harmful bacteria, viruses, or fungus to clean and/or sanitize the straw 150.

After fluid washing, one or more of the heating element 128 or drying assembly 170 may be operated to dry any fluid left in or on the straw 150 or channels 181 and 182. The heating element 128 may be a ceramic or other suitable heating element adapted to work in a wet or humid environment. The drying assembly 170 may comprise a fan assembly 171 comprising a fan 174 and having a fan inlet 173 and a fan outlet 172. The fan inlet 173 and outlet 172 may have a mesh or grille or other covering adapted to protect the fan 174. The fan 174 in the fan assembly 171 may be a "squirrel-cage" type blower fan or another suitable fan mechanism. The fan 174 may circulate air over and/or through the straw 150 to dry the straw. The fan 174 may also comprise and/or be operable with a heating element (e.g., 128) to heat air moved by the fan. Or a heating element otherwise provided in the case may be used for this purpose.

A device for mechanical cleaning of the straw 150 may also be provided. Mechanical or physical cleaning of the straw may be performed by the brush 160 which comprises a handle 161 and bristles 162. The brush 160 may be disposed for example in the channel 163 in the interior 180 which corresponds to the shape of the brush 160. The brush 160 may comprise metal wire or nylon bristles 162 and the handle 161 may be plastic or metal or any other suitable material.

According to one example, the brush may extend a distance corresponding to at least half the length of the straw. By sliding a first end of the straw over the brush, a first portion of the straw can be cleaned. By flipping the straw over and sliding the second end of the straw over the brush, a second portion of the straw can be cleaned.

Figure 2:
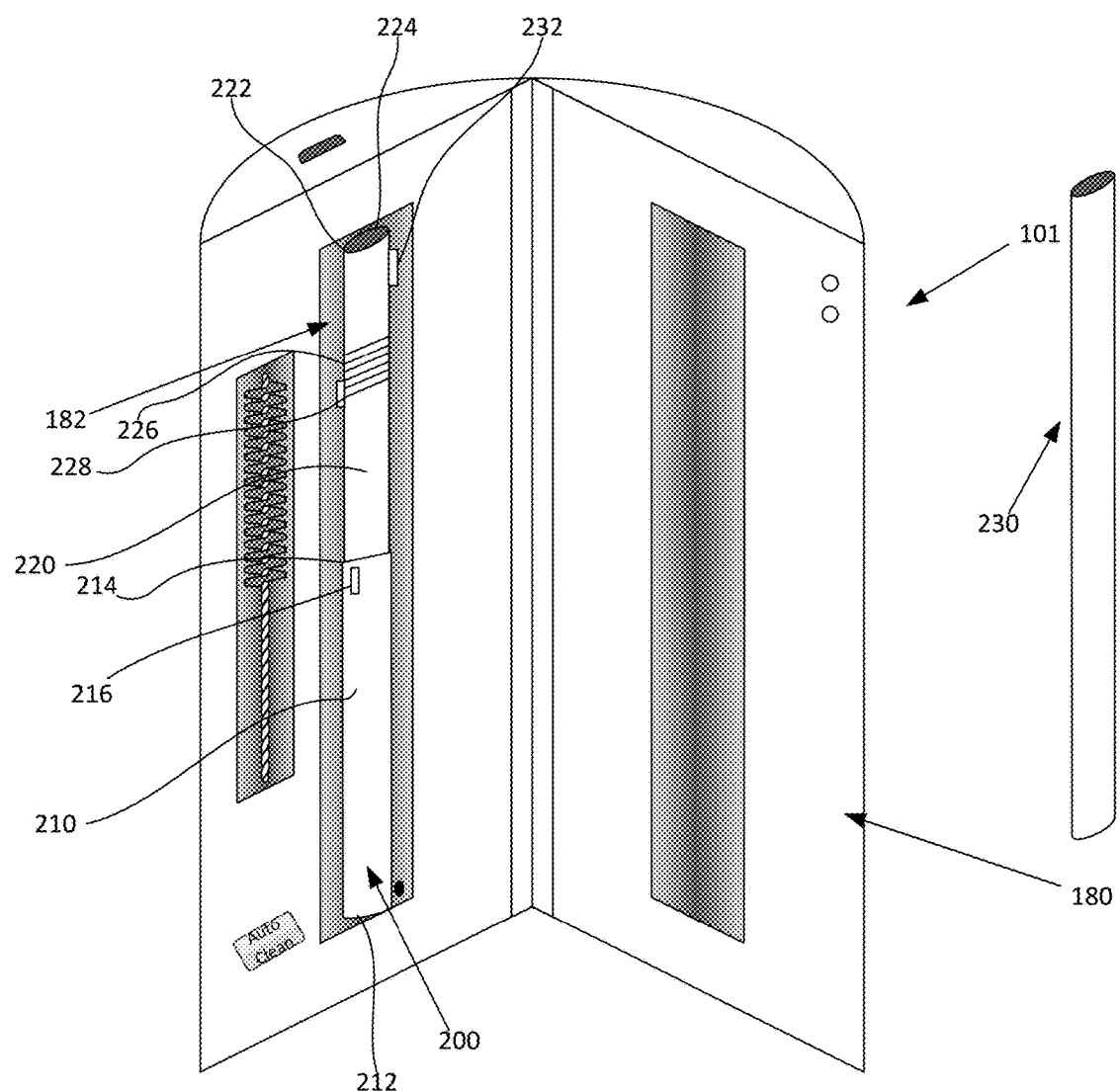

With reference now to FIG. 2, a top perspective view of an embodiment of a personal, reusable straw system 100 and a case 101 for the straw 200 is provided. The straw 200 is disposed in the first channel 182 of the interior 180 similar to the straw 150. However, the straw 200 is adapted to change in length and to change the angle of one of its portions relative to another of its portions. For example, the straw 200 may comprise a lower portion 210 and an upper portion 220. The lower portion 210 has an interior diameter slightly larger than the exterior diameter of the upper portion 220 such that the lower portion 210 may "telescope" over the upper portion 220 to vary the length of the straw 200. The lower portion 210 comprises a bottom end 212, a top end 214, and a locking mechanism 216. The top end 214 is adapted to slide over the exterior of the upper portion 220, and the locking mechanism 216 is adapted to lock the lower portion 210 in place relative to the upper portion 220 such as by friction, engagement with a locking tab, or other suitable means. The upper portion 210 comprises a top end 222 and has an interior diameter 224.

A flexible rubber, plastic, or silicone tubing may be placed in the interior diameter 224 to facilitate drinking fluids through the straw 200.

The upper portion 220 further comprises a bending assembly 226 adapted to permit the top end 222 of the straw to be rotated with respect to the rest of the upper portion 220 to form an angle therebetween. An angle lock 228 may be used to lock the relative angle between the top end 222 and the rest of the upper portion 220.

An insert 230 having an exterior diameter smaller than the interior diameter 224 of the straw 200 may be inserted into the straw 200 to provide for varying of the interior diameter of the straw 200 and is locked in place by the locking mechanism 232. Alternatively, a mouthpiece or other insert may be used to vary the shape of the straw 200 to provide for different drinking configurations. Other components from FIG. 1 may be included but are omitted in FIG. 2 for clarity and simplicity.

Figure 3:
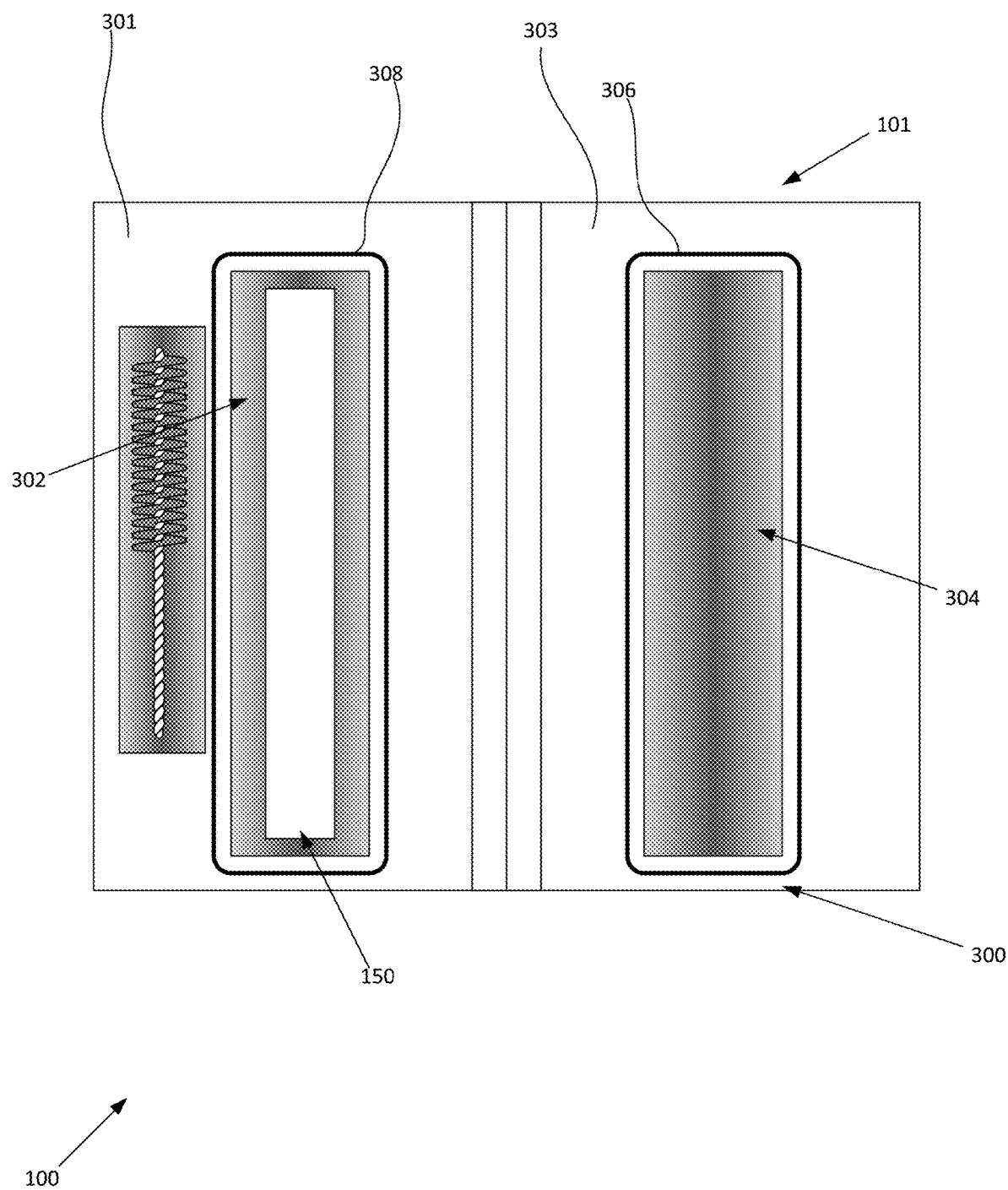
FIGS. 3-5 provide views of embodiments of interior configurations for the case and holder of the personal, reusable straw according to the present invention.

With reference now to FIG. 3, an embodiment of an interior 300 configuration for the case 101 of the personal, reusable straw 150 according to the present invention is provided. The interior 300 is similar to the interior 180 as shown in FIG. 1 except that one or more sealing assemblies 308 and 306 are disposed about the channels 302 and 304 on the surface of the respective first interior 301 and second interior 303 sides of the interior 300. The sealing assemblies 306 and 308 may be O-rings or other suitable sealing means for preventing the unwanted egress of fluid from the channels 302 and 304. These features may be included in other embodiments.

Figure 4:
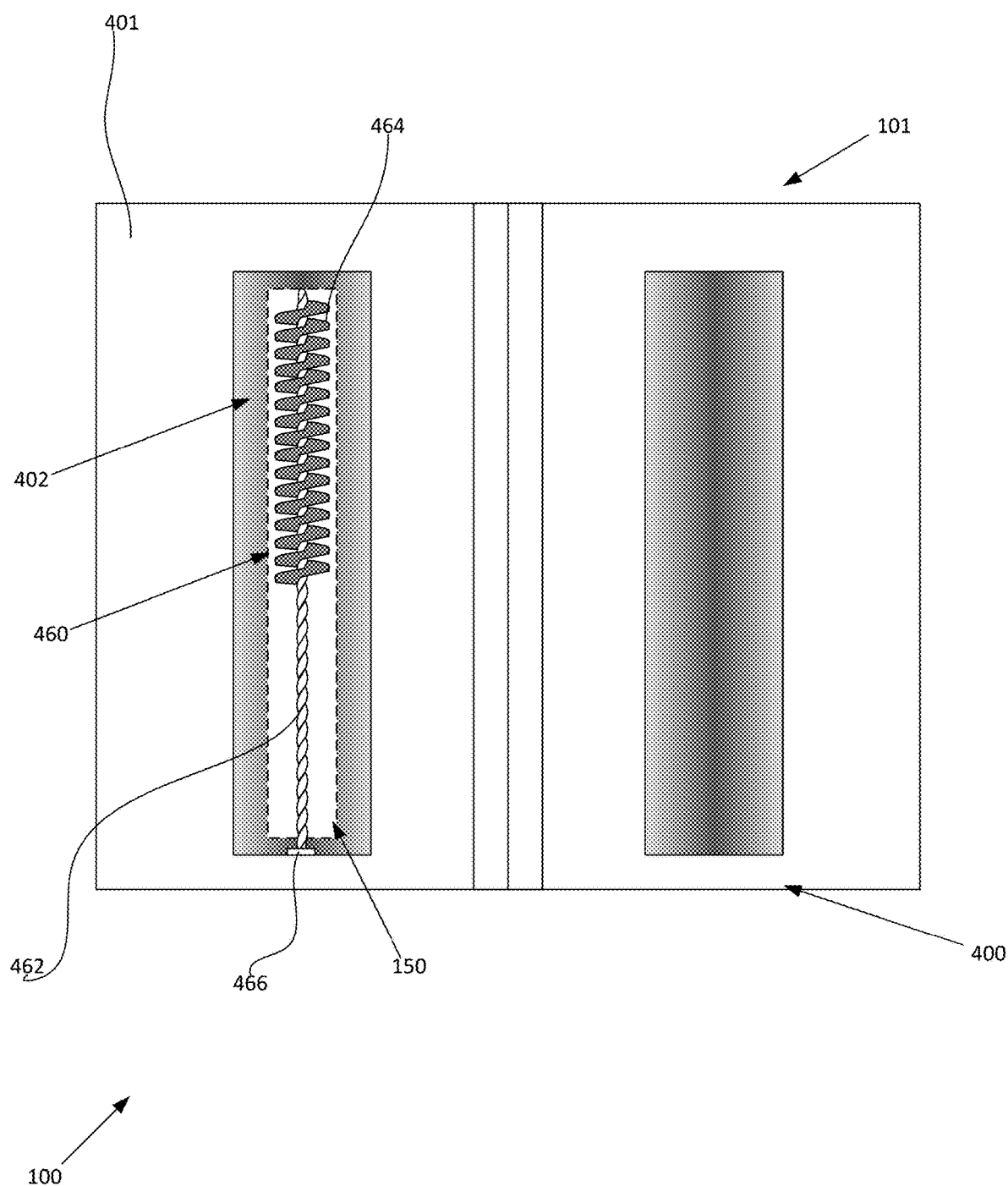

With reference now to FIG. 4, an embodiment of an interior 400 configuration for the case 101 of the personal, reusable straw 150 according to the present invention is provided. As shown in FIG. 4, the brush 460 is disposed within the straw 150. The brush 460 comprises a body 462 and bristles 464 and the end of the body 462 is secured to a hinging mechanism 466 at the bottom of the channel 402 on the first side 401. The brush 460 is adapted to either hinge or bend out at the hinging assembly 466 such that the straw 150 may be inserted over the brush 460, thereby facilitating a cleaning of the interior of the straw 150. The brush 460 is adapted to extend at least halfway through the length of the straw 150 such that the entire interior surface of the straw 150 may be cleaned by the brush 460. The straw 150 may be placed on the brush 460, removed, rotated 180 degrees, and placed on the brush 460 again to completely clean the interior of the straw 150.

Figure 5:
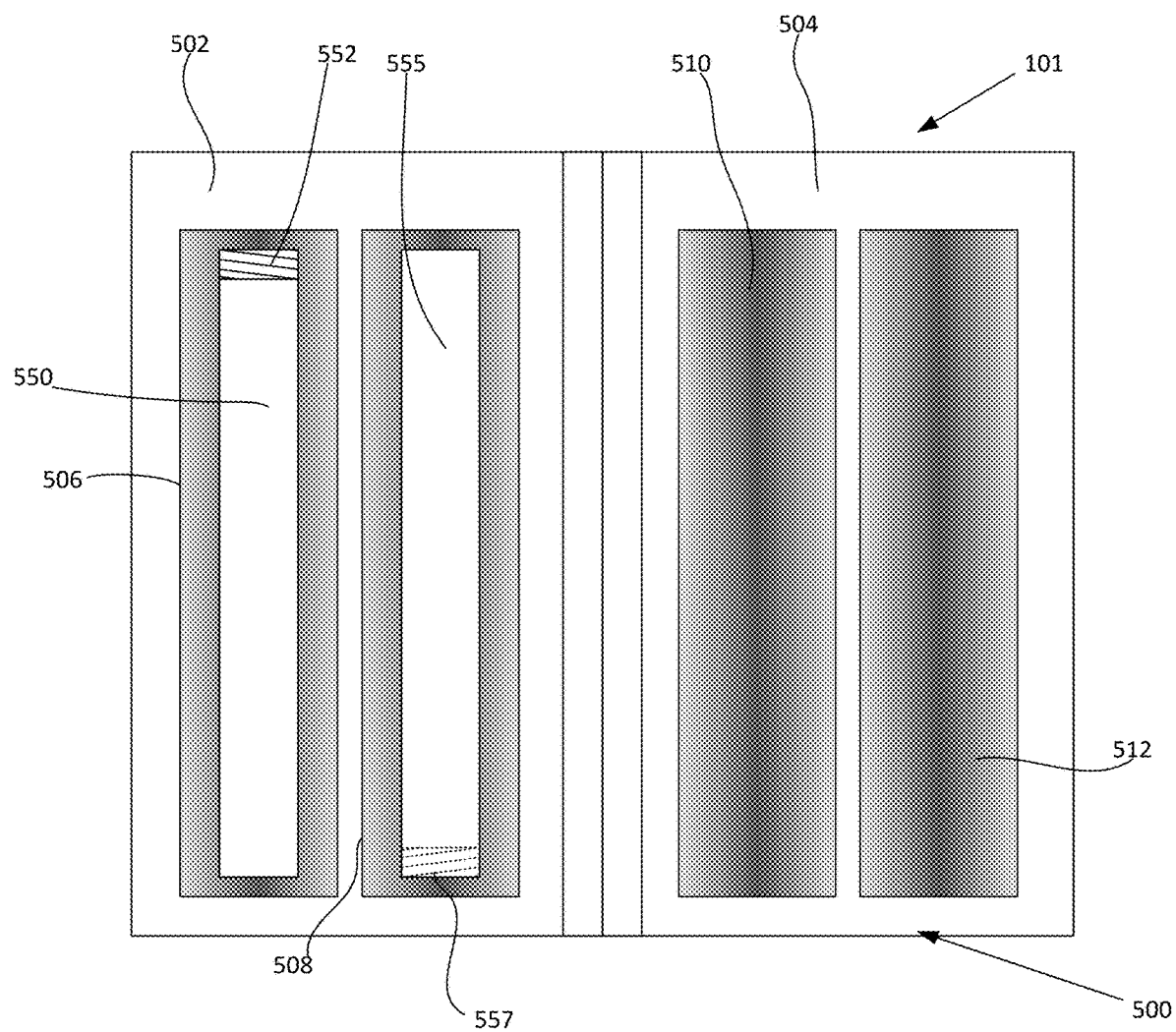

With reference now to FIG. 5, an embodiment of an interior 500 configuration for the case 101 according to the present invention is provided. The straw comprises a first portion 550 and a second portion 555 with the first portion 550 having an exterior threading 552 which corresponds to an interior threading 557 of the second portion 555 thereby permitting the two portions 550 and 555 to be threaded together to form a complete drinking straw. The two portion 550 and 555 may be stored in separate channels 506 and 508 in the first interior side 502 having corresponding channels 510 and 512 on the second interior side 504. All other components of the case 101 may also be present in the holder configurations shown in FIGS. 3-5.

Figure 6:
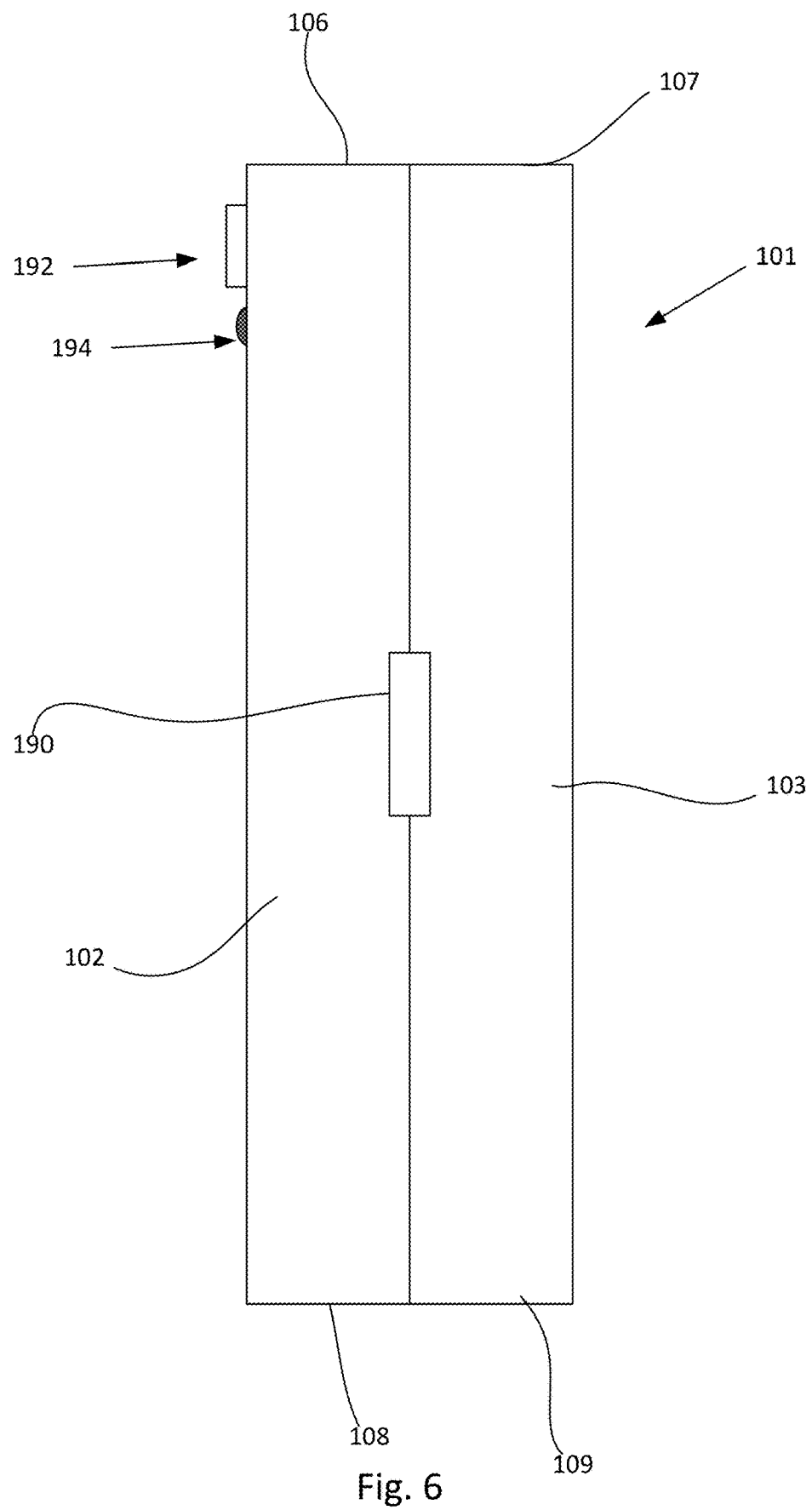
FIG. 6 provides a side view of an embodiment of the case for the personal, reusable drinking straw according to the present invention.

With reference now to FIG. 6 and FIG. 7, external side (FIG. 6) and top (FIG. 7) views of the case 101 are provided. A set of user operable elements 192 may be disposed on the exterior of side 102 of the case 101 to provide for user control of the electronics assembly 120 (shown in FIG. 1). The user operable elements 192 may comprise physical buttons, capacitive touch elements and/or other input mechanisms to provide for the control of the elements of the electronics assembly 120, including the ability to separately control the individual cleaning, heating, sanitizing and/or other elements. The input mechanisms may enable a user to turn individual elements on/off and/or control other characteristics of the elements. For example, the control for the fluid pump may control a flow mode (e.g., continuous flow or pulse mode), flow rate, flow duration, temperature of fluid and/or other flow characteristics. The control for the heating element may control the temperature, duration and other heating characteristics. The control for the sanitizing element may control the duration, intensity and other light characteristics.

One or more input mechanism may be operable to facilitate the ability for a user to program the operation for a group of elements. For example, the user can program the elements to be used in a programmed cycle, the order in which they are used, the duration of use for each element and/or other characteristics of the elements, for example those characteristics described elsewhere herein. The programs may be saved and stored. Different programs can be saved for different types of drinks. For example, user may create and store one program for water, another for juices (and/or specific types of juices), another for protein shakes, etc. The different programs can be customized to reflect the different cleaning, drying and/or sanitizing needed depending on the characteristics of the drink type. The programming and/or controls may be implemented via input mechanisms on the case, via a mobile application in communication with the case or otherwise.

One or more display elements and/or other visual indicators 194 may be present on the exterior of side 102 to provide visual feedback to a user. The visual indicators 194 may comprise LED elements, an OLED display, or other suitable visual feedback mechanisms. The visual indicators 194 may separately display the status of each or any element of the case, or can display a programmed sequence such as a status sequence. The visual indicators 194 can also display an amount of time remaining to finish cleaning, drying and/or sanitizing, or any other information relevant to the status of the case or any element of the case.

Audio indicators (not shown), such as a speaker, may also be used. A latching device 190 may be present on the exterior of the case 101 to secure the first side 102 and second side 103 together and to permit access to the interior 180 of the case 101.

The physical configuration of the case and locations of the straw, straw holder and various other elements as described above are for example only. Other physical configurations and arrangements may be used.

With reference now to FIG. 8, a block diagram of a case 800 and external device 850 according to the present invention are provided. The case 800 comprises a straw holder 802, a fluid flushing and washing system or fluid system 810, a power system 820, and a logic system 830. The power system 820, logic system 830, and electrical elements of the fluid system 810 are in electrical communication with other elements via the logic bus 831 and receive power through the power bus 821. The logic bus 831 and power bus 821 may be a single bus or may be one or more busses through which elements of the case 800 transmit and/or receive power and/or communications signals.

Within the holder 802 a light source 804, which may be UV or other light source having one or more lenses or emitters, is positioned to provide UV light within the holder 802. A first reflector 806 and a second reflector 808 may be positioned at respective first and second ends of the holder 802 to reflect light throughout the holder 802 and any straw positioned or held therein. Alternatively, the entire interior surface of the holder 802 may be reflective.

Figure 9:
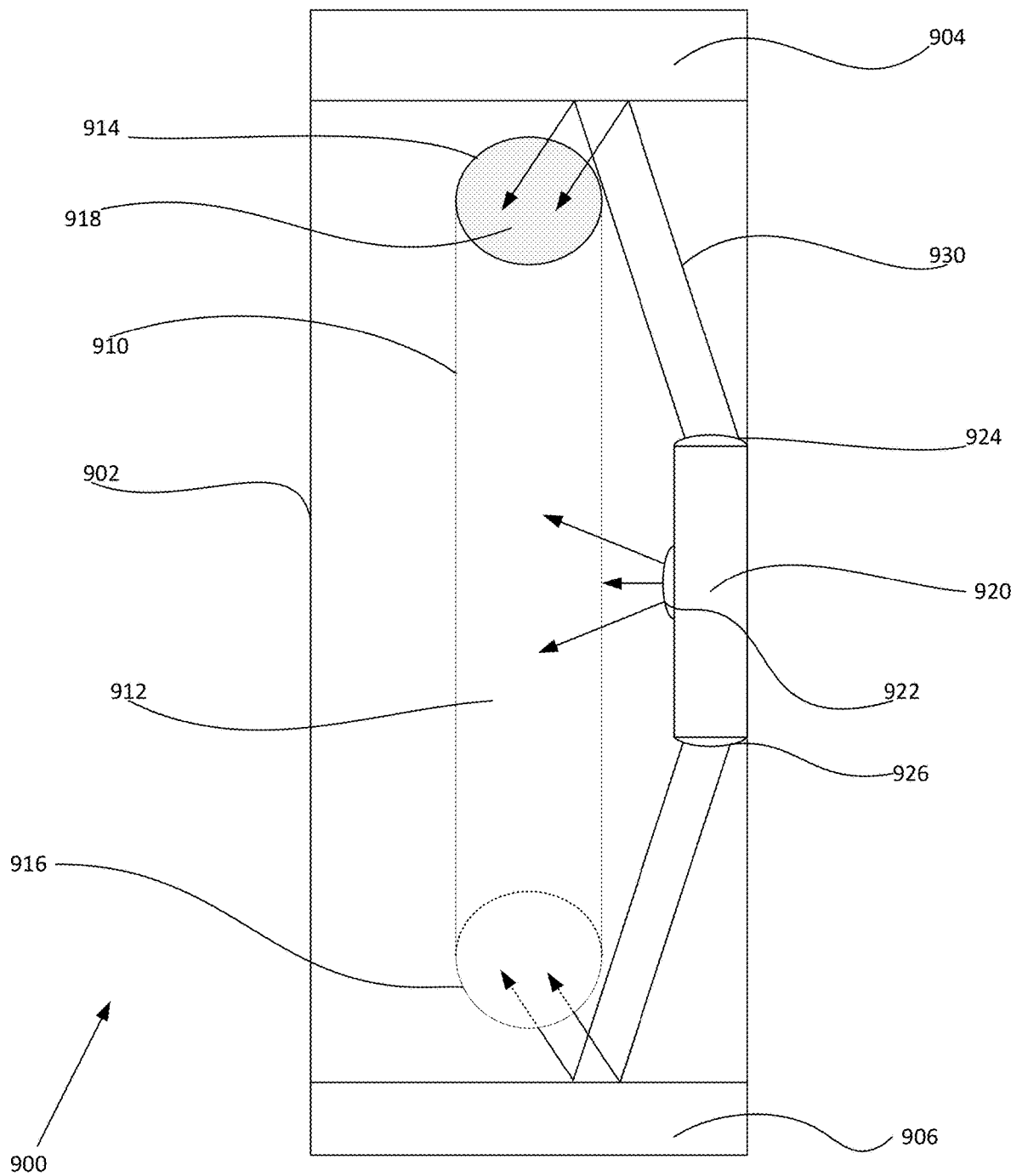
FIG. 9 provides a diagram of a UV light cleaning and sterilizing system for the holder of the personal, reusable drinking straw according to the present invention.

Additional detail is provided in FIG. 9. As shown in the UV light cleaning and sterilizing system 900 of FIG. 9, a straw 910 positioned in a holder 902 may be cleaned and/or sterilized by a light source 920 positioned in the holder 902. The light source 920 may be a UV or other light source capable of emitting radiation for cleaning and/or sterilizing the straw 910. The light source 920 may have a set of light emitters such as a first emitter 922, second emitter 924, and third emitter 926 capable of emitting light or radiation in one or more directions through corresponding lenses, apertures, or by an elongated light source. Light 930 emitted by the light source 920 may directly strike or reach the outer surface 912 of the straw 910. However, a set of one or more reflectors such as the first reflector 904 and the second reflector 906 may be used to purposefully direct sufficient light (e.g., reflect or bounce the light) into the interior 918 of the straw 910 via the first opening 914 and second opening 916 as shown to fully clean and/or sterilize the interior of the straw 910.

With reference back to FIG. 8, the fluid system 810 may comprise a fluid reservoir 811, a pump 812, a heater 813, a spent fluid reservoir 816, a filter 817 and/or other elements. Fluid in the fluid system 810 is held in the reservoir 811 and is pumped by the pump 812 (optionally through or in proximity to the heater 813) and the fluid ingress tube 814 into the holder 802 where it washes or flushes a straw held therein. The fluid continues through the fluid egress tube 815 where it may then be held in the spent fluid reservoir 816. In some embodiments the spent fluid may be cleaned or filtered by the filter 817 and returned to the reservoir 811 for re-use. The filter 817 may be any suitable filter such as a fine mesh filter, a reverse osmosis filter, or an activated charcoal filter. A fan 840, which may comprise a heating element, is used to send air through the fan air channel 842 into the holder 820 to dry the straw therein after use or after flushing and/or washing by the fluid system 810.

Control of the elements of the fluid system 810 and the fan 840, as well as the user interface 835 and display 836, is provided by the controllers 832. The controllers 832 may be any suitable microprocessor, system-on-a-chip, or microcontroller capable of controlling the elements of the case 800. One or more configurations, firmware, functions, or instructions sets may be stored on the memory 833 for use by the controllers 832 in operating the electrical elements of the case 800. The user interface 835 may comprise one or more user interface elements such as physical buttons, touch screen controls, a microphone for voice control, or other user operable elements for controlling the functions of the case 800. The current status of the case 800, including the battery 822 status, operation status, program status, program duration, and current mode of operation may be displayed din the display 836. The display 836 may be an LED, OLED, or other suitable display capable of providing visual feedback to a user. The electrical components may be provided power by an onboard battery 822 which may be a nickel-cadmium battery (NiCad), nickel-metal hydride (NiMH), lithium ion (Li-ion), or other suitable battery type. Charging and discharging of the battery 822, such as through the charging port 823 which may be a pin-and-barrel connector, USB type A, B, or C connector, or other suitable connector type, is controlled by the controllers 832 to regulate the charge, temperature, and discharge rate of the battery 822 over the power bus 821.

Additionally, the case 800 may communicate wirelessly via the wireless transceiver 834 via Bluetooth, Wi-Fi, near-field communications ("NFC"), or other suitable wireless radio protocols with an external device 850 via the external device 850 wireless transceiver 856. The external device 850 may be a specially programmed device or may be a handheld computing device such as a cellular telephone, tablet, or laptop running special purpose computer software or an application for controlling the case 800. Control of the case 800 may be provided through an application ("app") configured to provide a set of user interface controls in the user interface 852 shown in the display 854 of the external device 850. Exemplary screenshots and functions are provided in FIGS. 10 and 11.

Figure 10:
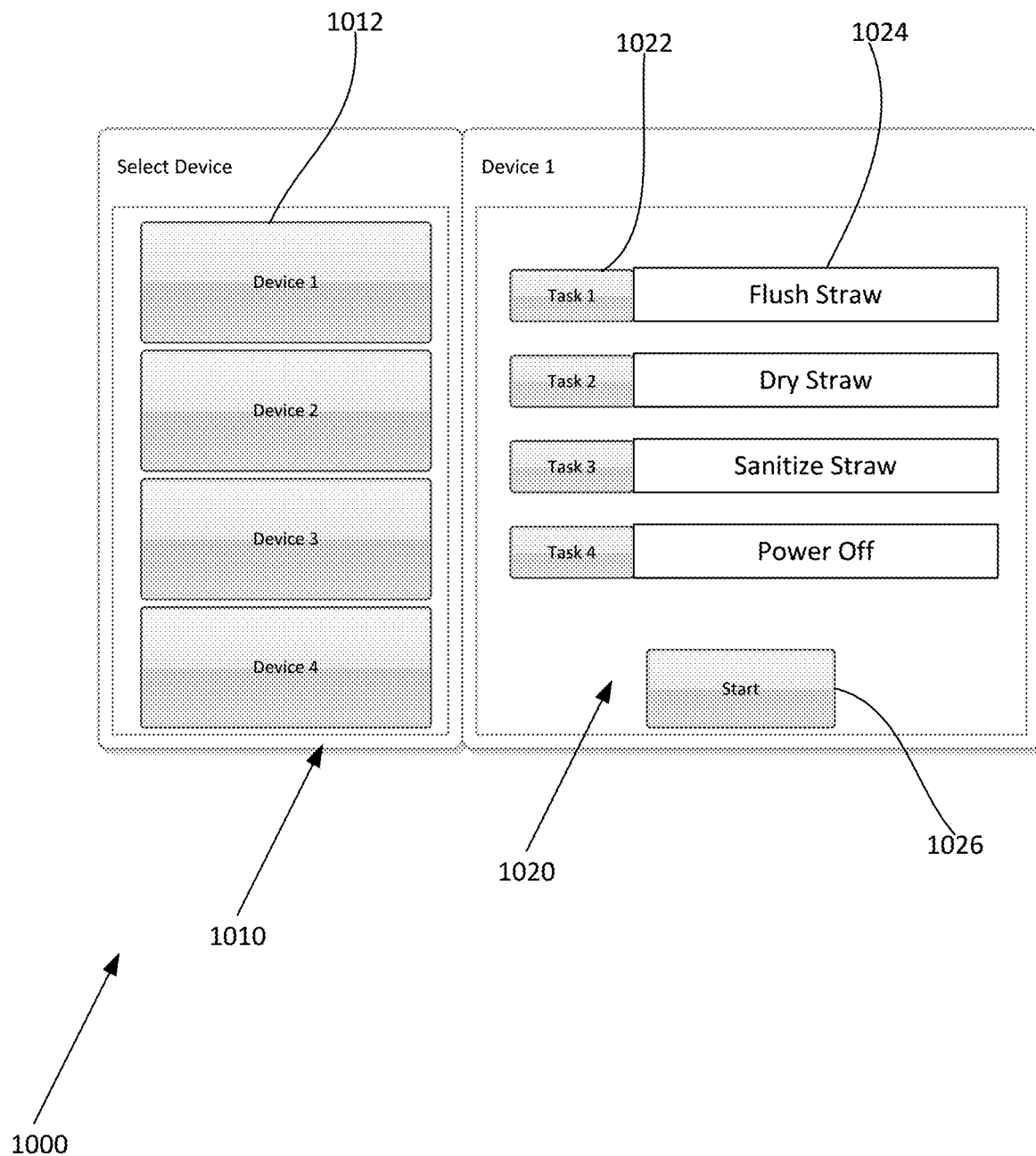
FIGS. 10 and 11 provide diagrams of a user interface comprising user interface controls for operating functions of the case of the personal, reusable drinking straw according to the present invention.
Figure 11:
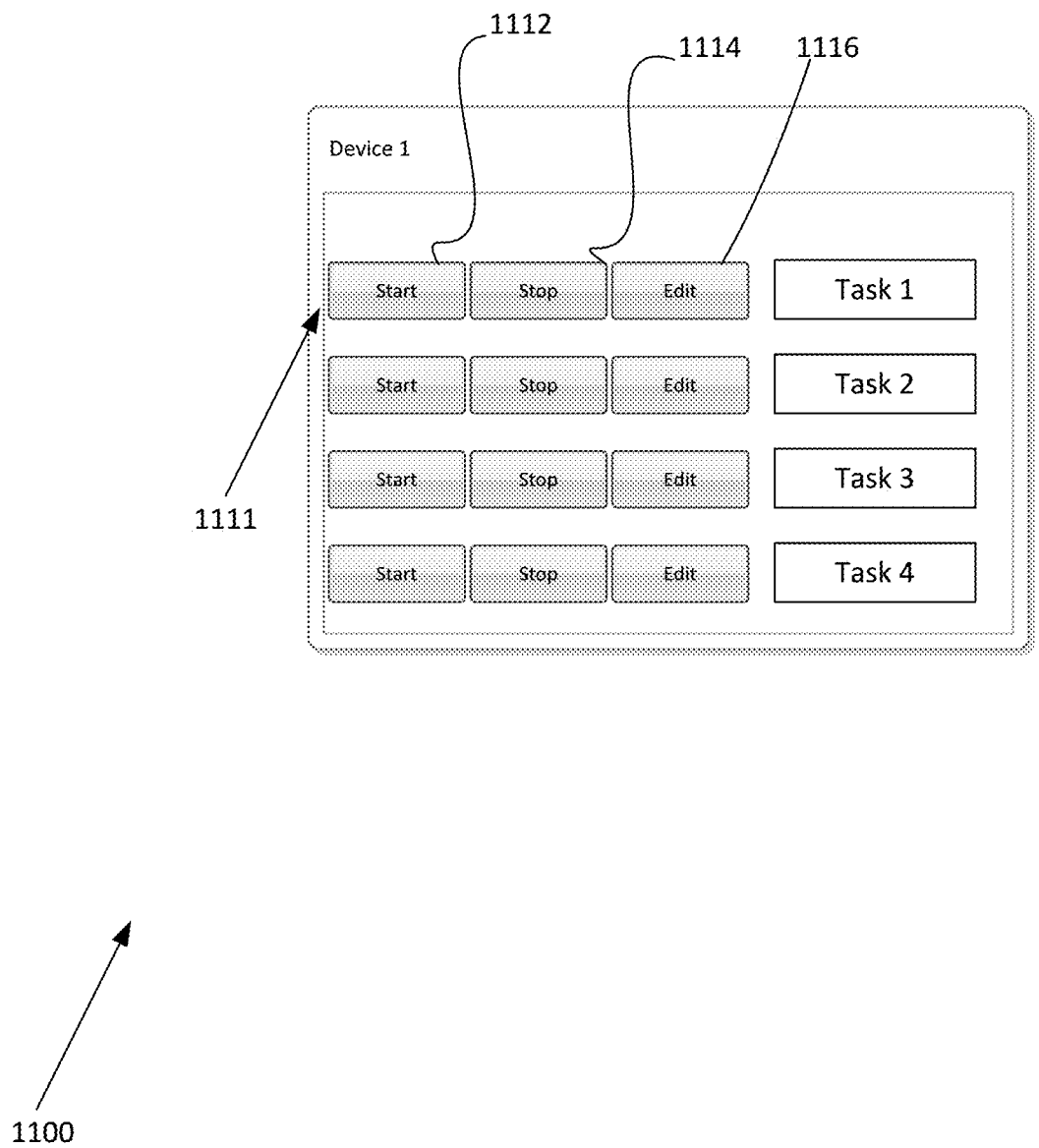
Figure 12:
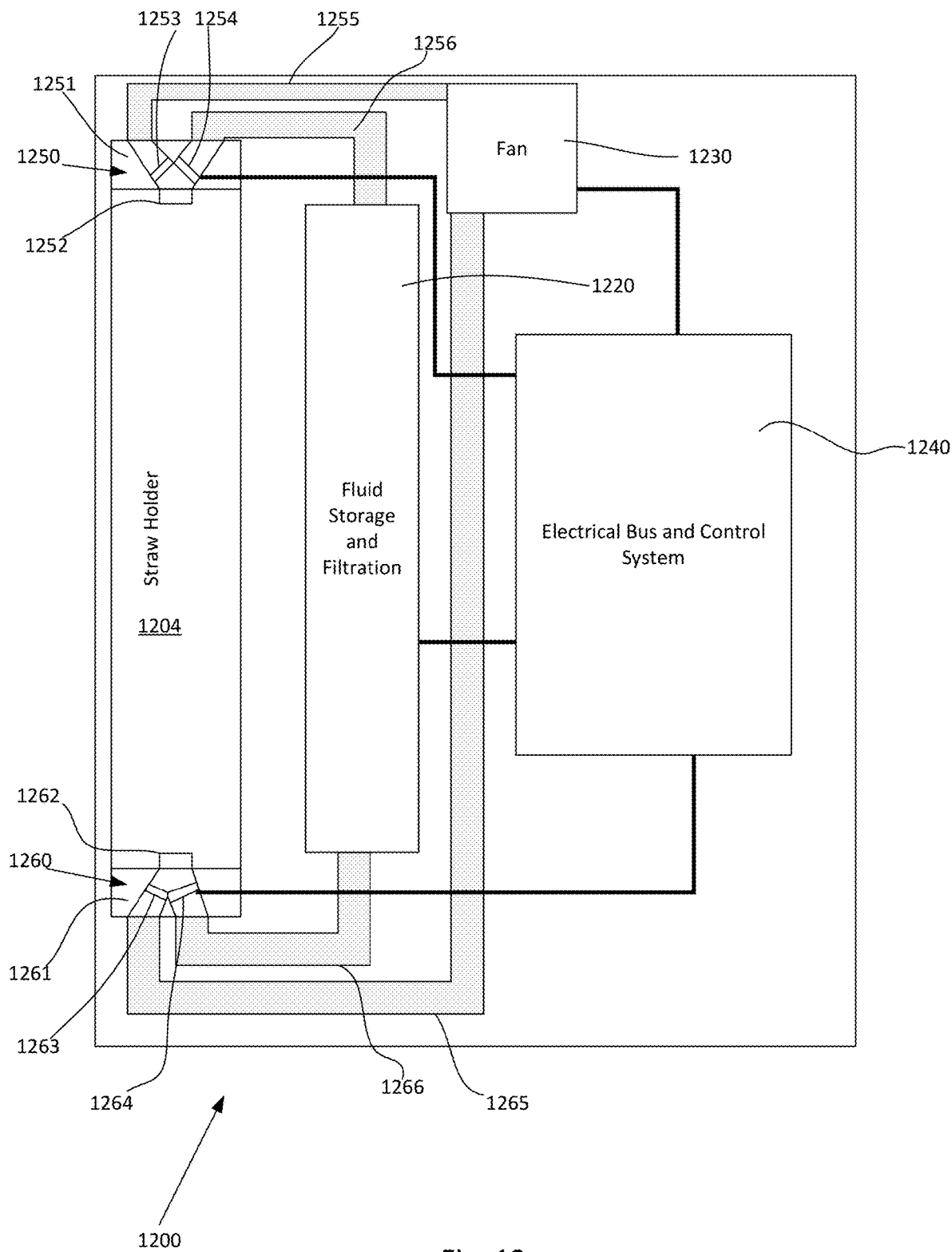
FIG. 12 provides a block diagram view of the case and holder for the personal, reusable drinking straw according to the present invention.

With reference now to FIGS. 10 and 11, user interfaces comprising user interface controls or control elements for providing inputs to the controller or holder and for viewing information are provided. FIG. 10 provides screenshots of an application interface 1000 comprising a device selection interface 1010, a task or program customization interface 1020, and FIG. 11 provides screenshots of a task or program control and execution interface 1100 are provided. The application interface 1000 may be displayed on an internal display of the case and/or may be provided in a set of graphical user interfaces and user interface elements generated by an application of a remote device in communication with the case. The device selection interface 1010 provides for the selection of a device, such as the case 100 of FIG. 1 or the case 800 of FIG. 8, and for the control of tasks or programs associated with that device. A device may be selected using the device selection controls 1012. When a device is selected, such as a first device named "Device 1", tasks or programs related to that device may be run, or the user may customize or configure elements of the device including the tasks or programs. The program customization interface 1020 enables user customization of a program to be run, using start control 1026, on the device. The program may comprise one or more tasks selectable by a task control 1022 and as described in the description 1024. The user may set parameters for any given task such as the duration of the task, the time when the task is to be run, and the frequency the task is to be run. The user may also configure the program, or an individual task, to run at a certain location, to run based on a certain beverage consumed by the user using a straw in the device, i.e., case, or at a certain time of day. Other configurable parameters may include the temperature of the fluid for flushing and/or washing, whether fluid is to be re-used, filtered, and/or stored, and the temperature and duration of drying by a fan. After a program or individual task has been configured using the program configuration interface 1020, a program or individual task may be run using the task or program control and execution interface 1110. Using the interface 1100, an individual task or complete program 1111 may be started 1112, stopped 1114, or edited 1116 using the user interface controls within the interface.

The case 800 as shown in FIG. 8 may also comprise additional elements such as haptic feedback devices, vibration motors, sound control chips, speakers, gyroscopes, and accelerometers that may be controlled by the controller 832 and configured using the user interface 835 or external device 850 to provide for additional control and customization over the case 800.

With reference now to FIG. 11, a block diagram of a case 1200 comprising a set of microvalve-controlled conduits is provided. The case 1200 comprises a straw holder 1204, a fluid storage and filtration system 1220, a fan system 1230, and an electrical bus and control system 1240. The fluid storage and filtration system 1220 may comprise one or more elements of the fluid system 810 of FIG. 8 and the electrical bus and control system 1240 may comprise one or more elements of the power system 820 and control system 830 of FIG. 8. The holder 1204 further comprises an upper manifold assembly 1250 and a lower manifold assembly 1260. In the upper manifold system 1250 a fan inlet conduit 1255 leads from the fan 1230 to the manifold 1251 and the fluid inlet conduit 1256 leads from the fluid storage and filtration system 1220 to the manifold 1251. The output of the manifold 1251 is the output 1252 which may be a conduit, nozzle and or other structure that is inserted into and/or around an end of a reusable straw. The manifold 1251 comprises one or more microvalves 1253 and 1254 controlled by the control system 1240 to selectively control the fluid paths operable therethrough. For example, one conduit 1256 may lead from the fluid storage and filtration system 1220 to provide fluid to the straw. Another conduit 1255 may lead air (e.g., from the fan 1230) to the straw for drying the outside and/or inside of the straw. The microvalves 1253 and 1254 may be open or closed and operate to control the flow of fluids or air into the straw via the output 1252. A complimentary lower manifold system 1260 is provided at the output end of the straw to selectively lead fluid back to the fluid storage and filtration system 1220 without allowing air to flow thereto. In the lower manifold system 1260 a fan outlet conduit 1265 leads from the manifold 1261 to the fan 1230 and the fluid outlet conduit 1266 leads from the manifold 1261 to the fluid storage and filtration system 1220. The inlet for the manifold 1261 is the inlet 1262 which may be a conduit, nozzle and or other structure that is inserted into and/or around an end of a reusable straw. The manifold 1261 comprises one or more microvalves 1263 and 1264 controlled by the control system 1240 to selectively control the fluid paths operable therethrough.

The present invention is not to be limited in scope by the specific embodiments described herein. It is fully contemplated that other various embodiments of and modifications to the present invention, in addition to those described herein, will become apparent to those of ordinary skill in the art from the foregoing description and accompanying drawings. Thus, such other embodiments and modifications are intended to fall within the scope of the following appended claims. Further, although the present invention has been described herein in the context of particular embodiments and implementations and applications and in particular environments, those of ordinary skill in the art will appreciate that its usefulness is not limited thereto and that the present invention can be beneficially applied in any number of ways and environments for any number of purposes or in any number of markets. Accordingly, the claims set forth below should be construed in view of the full breadth and spirit of the present invention as disclosed herein

The invention claimed is:

1. A case for a straw, the case comprising:
   a. an outer case portion and an inner holder, the inner holder comprising:
      i. an inner portion, having a channel therein, configured to conform to the contour of the straw; and
      ii. at least one mechanism located therein to clean, dry and/or sanitize the straw when located within the holder.

2. The case of claim 1, the case comprising a cleaning mechanism.

3. The case of claim 1, the case comprising a drying mechanism.

4. The case of claim 1, the case comprising a sanitizing mechanism.

5. The case of claim 1, the case comprising a sanitizing mechanism comprising a light source and one or more reflectors positioned and configured to reflect light to the inner surface of the straw.

6. The case of claim 1, the case comprising a sanitizing mechanism comprising a light source positioned and configured to irradiate an outer surface of the straw and one or more reflectors positioned and configured to reflect light to the inner surface of the straw.

7. The case of claim 1, the case comprising a cleaning mechanism and a drying mechanism.

8. The case of claim 1, the case comprising a cleaning mechanism and a sanitizing mechanism.

9. The case of claim 1, the case comprising a drying mechanism and a sanitizing mechanism.

10. The case of claim 1, the case comprising a cleaning mechanism and a brush.

11. The case of claim 1, the case comprising a cleaning mechanism, including a fluid reservoir and a pump.

12. The case of claim 1, the case comprising a cleaning mechanism, including a fluid reservoir and a pump configured to circulate a fluid through a straw located within the case.

13. The case of claim 1, the case comprising a drying mechanism including a heating element.

14. The case of claim 1, the case comprising a drying mechanism including an air circulating element configured to circulate air within the inner holder.

15. The case of claim 1, the case comprising a drying mechanism including an air circulating element configured to circulate air within the inner holder and a heating element to heat the air.

16. The case of claim 1, the case comprising a sanitizing mechanism including a UV light source within the case to sanitize the straw located within the inner holder.

17. The case of claim 1, the case comprising a manifold configured to lead fluid to the straw.

18. The case of claim 1, the case comprising a manifold configured to lead fluid to the straw, the manifold having at least two fluid flow portions, one portion configured to direct fluid around the outer surface of the straw and one portion configured to direct fluid through the straw.

19. The case of claim 1, the case comprising a manifold configured to lead fluid to the straw, the manifold having at least two fluid flow portions, one portion configured to direct fluid into and/or around the outer surface of the straw and one portion configured to direct air into and/or around the straw.

20. The case of claim 1 comprising a programmable controller for controlling one or more mechanisms in the case and comprising a wireless transceiver for communicating with a mobile application, the mobile application comprising:
- a first display portion for presenting options for a user to select at least one of the mechanisms;
- a second display portion for presenting options for a user to select parameters associated with a one or more tasks for the at least one selected mechanism; and
- a third display portion for presenting options for a user to start, stop or edit a task.

* * * * *